(12) United States Patent
Martin et al.

(10) Patent No.: US 10,149,678 B1
(45) Date of Patent: Dec. 11, 2018

(54) SUTURING INSTRUMENT WITH ELASTOMERIC CLEAT

(71) Applicant: Ethicon Endo-Surgery, LLC, Guaynabo, PR (US)

(72) Inventors: David T. Martin, Milford, OH (US); Christopher J. Hess, Cincinnati, OH (US); William J. White, West Chester, OH (US); Aaron J. Brickner, Milford, OH (US); Daniel J. Prenger, Loveland, OH (US); Frederick E. Shelton, IV, Hillsboro, OH (US); Adam Hensel, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 545 days.

(21) Appl. No.: 14/741,579

(22) Filed: Jun. 17, 2015

(51) Int. Cl.
*A61B 17/04* (2006.01)

(52) U.S. Cl.
CPC ...... *A61B 17/0469* (2013.01); *A61B 17/0491* (2013.01); *A61B 17/0482* (2013.01); *A61B 2017/047* (2013.01)

(58) Field of Classification Search
CPC ........ A61B 17/06061; A61B 17/06114; A61B 17/0469; A61B 17/0482; A61B 17/0483; A61B 17/0491; A61B 17/3498; F16G 11/105; F16G 11/10; B63B 21/08; A61M 39/06
See application file for complete search history.

(56) References Cited

U.S. PATENT DOCUMENTS

| | | | | |
|---|---|---|---|---|
| 5,141,491 A | * | 8/1992 | Bowald | A61B 17/320016 604/22 |
| 5,443,452 A | * | 8/1995 | Hart | A61B 17/3498 137/849 |
| 5,911,727 A | * | 6/1999 | Taylor | A61B 17/0491 606/139 |
| 6,015,428 A | * | 1/2000 | Pagedas | A61B 17/0483 606/232 |
| 6,607,542 B1 | * | 8/2003 | Wild | A61B 17/122 606/139 |
| 7,993,354 B1 | * | 8/2011 | Brecher | A61B 17/0482 606/145 |
| 8,702,732 B2 | | 4/2014 | Woodard et al. | |
| 9,168,037 B2 | | 10/2015 | Woodard et al. | |
| 9,357,998 B2 | | 6/2016 | Martin et al. | |
| 9,375,212 B2 | | 6/2016 | Martin et al. | |
| 9,474,522 B2 | | 10/2016 | Deck et al. | |

(Continued)

*Primary Examiner* — Christopher L Templeton
(74) *Attorney, Agent, or Firm* — Frost Brown Todd LLC

(57) ABSTRACT

A surgical instrument that has a cartridge receiving assembly, a shaft assembly, and a needle driving cartridge. The cartridge receiving assembly in connected to the shaft assembly. The needle driving cartridge is capable of being inserted into the cartridge receiving assembly. The needle driving cartridge is capable of driving a needle along an orbital path in a single angular direction. The needle driving cartridge includes a body, a curved needle, a needle drive assembly, and a needle guide assembly capable of guiding a needle along the orbital path. The needle guide assembly includes a cleat. The cleat has two needle engagement features. The two needle engagement features are configured to simultaneously engage two separate regions of the outer surface of the needle at the same portion of the length of the needle.

18 Claims, 11 Drawing Sheets

(56) References Cited

U.S. PATENT DOCUMENTS

| | | | |
|---|---|---|---|
| 2006/0030868 A1* | 2/2006 | Bennett, III | A61B 17/0057 606/148 |
| 2006/0111732 A1* | 5/2006 | Gibbens | A61B 17/0482 606/145 |
| 2006/0281970 A1* | 12/2006 | Stokes | A61B 1/00087 600/104 |
| 2006/0282098 A1* | 12/2006 | Shelton, IV | A61B 1/00087 606/144 |
| 2007/0239176 A1* | 10/2007 | Stokes | A61B 17/00234 606/144 |
| 2008/0132919 A1* | 6/2008 | Chui | A61B 17/0482 606/145 |
| 2010/0042116 A1* | 2/2010 | Chui | A61B 17/0482 606/145 |
| 2012/0143248 A1* | 6/2012 | Brecher | A61B 17/0482 606/223 |
| 2014/0031864 A1* | 1/2014 | Jafari | A61B 17/0401 606/232 |

* cited by examiner

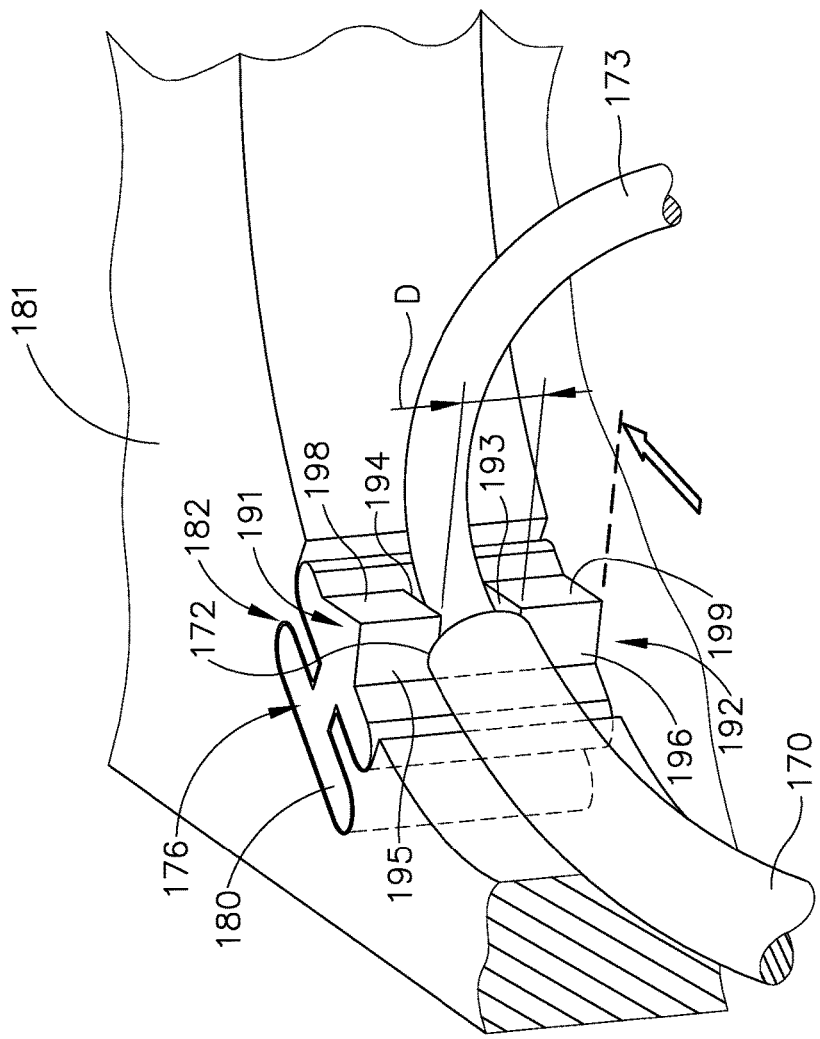

SUTURING INSTRUMENT WITH ELASTOMERIC CLEAT

BACKGROUND

Sutures may be used in a wide variety of surgical procedures. Manual suturing may be accomplished by the surgeon using a fine pair of graspers to grab and hold a suture needle, pierce the tissue with the needle, let go of the needle, and re-grasp the needle to pull the needle and accompanying suture thread through the tissues to be sutured. Such needles may be curved with the suture attached to the trailing end of the needle.

Some surgical instruments automate at least part of the suturing procedure. Examples of automated suturing instruments are described in U.S. Pat. No. 8,702,732, entitled "Laparoscopic Suturing Instrument with Dual-Action Needle Graspers," issued Apr. 22, 2014, the disclosure of which is incorporated by reference herein; U.S. Pub. No. 2011/0313433, entitled "Laproscopic Suture Device with Asynchronous In-Line Needle Movement," published Dec. 22, 2011, now U.S. Pat. No. 9,168,037, issued Oct. 27, 2015, the disclosure of which is incorporated by reference herein; U.S. Pub. No. 2014/0171970, entitled "Circular Needle Applier with Articulating and Rotating Shaft," published Jun. 19, 2014, now U.S. Pat. No. 9,357,998, issued Jun. 7, 2016, the disclosure of which is incorporated by reference herein; and U.S. patent application Ser. No. 14/297,993, entitled "Jawed Cartridge Receiving Assembly for Needle Cartridge," filed Jun. 6, 2014, now U.S. Pat. No. 9,474,522, issued Oct. 25, 2016, the disclosure of which is incorporated by reference herein.

While various kinds of suturing instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 8C depicts an enlarged perspective view of the cleat of FIG. 8A, with a blunt end of the needle engaging the cleat.

Figure 1:
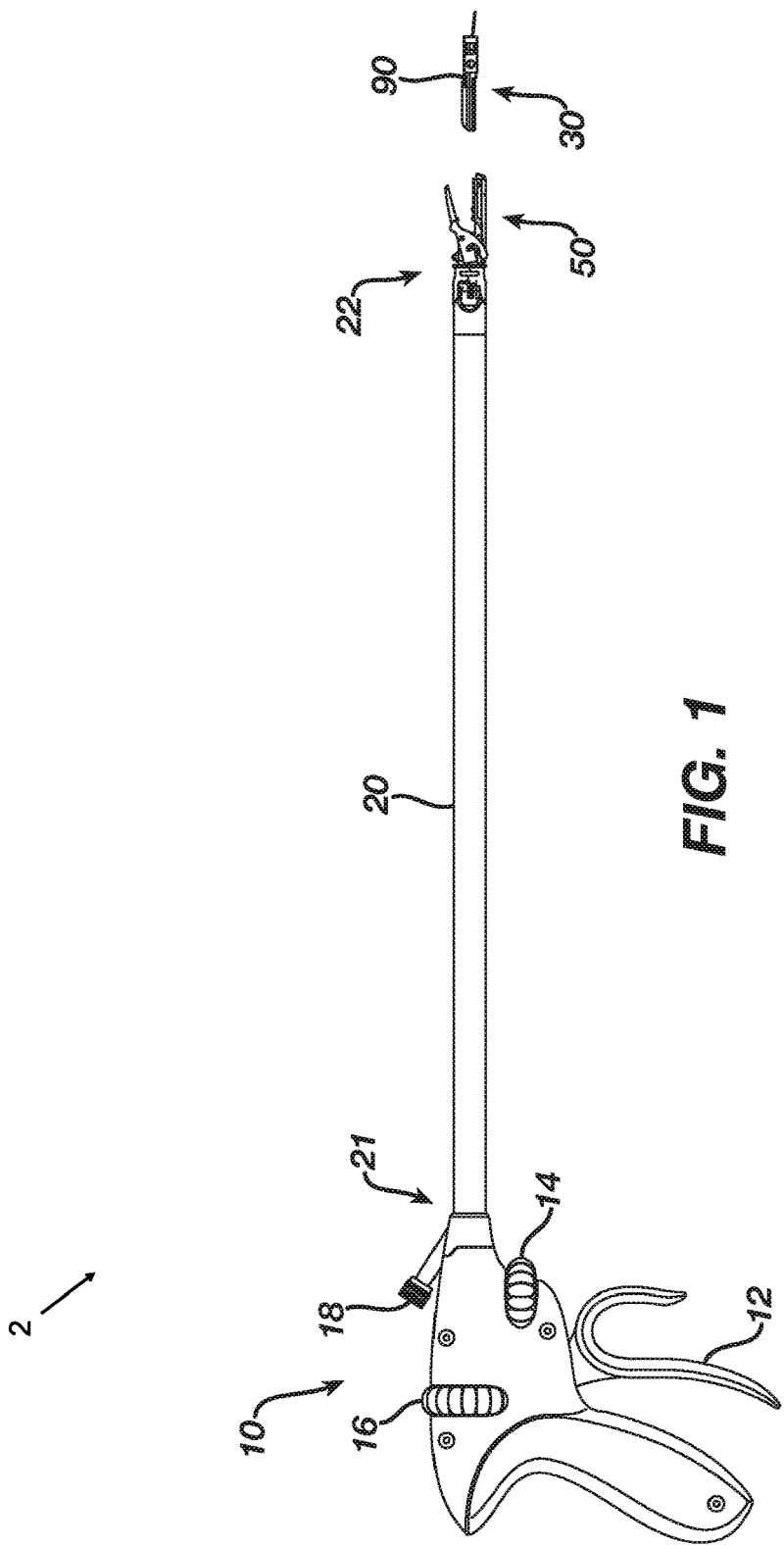
FIG. 1 depicts a side view of an exemplary surgical suturing instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Surgical Suturing Instrument

FIG. 1 illustrates an example of a surgical suturing instrument (2). Instrument (2) comprises a handle assembly (10), an elongate shaft (20), and a cartridge receiving assembly (50), which is operable to receive a needle applier cartridge (30). Shaft (20) has a proximal end (21), a distal end (22), and a longitudinal axis extending therebetween. Handle assembly (10) is connected to the proximal end (21) of the shaft (20). In this example handle assembly (10) is a manual pistol grip handle. However, a variety of other manual actuators could also be used, including but not limited to a scissor grip handle, a syringe grip handle, endoscopic rotary knobs, and the like. Handle assembly (10) could also take the form of a robotic interface, such as a DAVINCI puck, or a housing comprising gears or pulleys, servomechanisms, and the like.

Needle applier cartridge (30) is connected to the distal end (22) of shaft (20) via cartridge receiving assembly (50). Needle applier cartridge (30) is operable to rotate an arced needle in a circular path enabling a surgeon to selectively apply sutures. In some alternative versions, needle applier cartridge (30) is integral with shaft (20) and handle assembly (10) as a unitary disposable instrument intended for a single surgical procedure. Needle applier cartridge (30) may also be integral with shaft (20) and handle assembly (10) as a reusable instrument. Optionally, as illustrated here, needle applier cartridge (30) may be provided in a disposable cartridge body (90) and shaft (20) includes cartridge receiving assembly (50) to releasably hold cartridge body (90). In some such versions, shaft (20) and handle assembly (10) may also be disposable or reusable. Versions with reusable components are intended to be cleaned, sterilized, and reused for a multiple surgical procedures, and may include a flush port (18) to facilitate cleaning. The preferable life cycle of a reusable instrument is at least 50 operations, more preferably at least 150 operations, and most preferably at least 200 operations. Reusable components may be built using materials that can withstand autoclave sterilization temperatures of at least 135 degrees Celsius, although low temperature materials can also be used with low temperature sterilization techniques known in the art.

A first input (12), shown here as a trigger that pivots between opened and closed positions, may be used to selectively actuate needle applier cartridge (30). The trigger may be spring biased to return the trigger to its open position. A second input (14), shown here as a rotary knob, may be used to selectively articulate shaft (20). A third input (16), shown here as a rotary knob, may be used to selectively rotate needle applier cartridge (30) about shaft (20). Of course, the number, type, configuration, and operation of inputs (12, 14, 16) may vary.

Figure 2A:
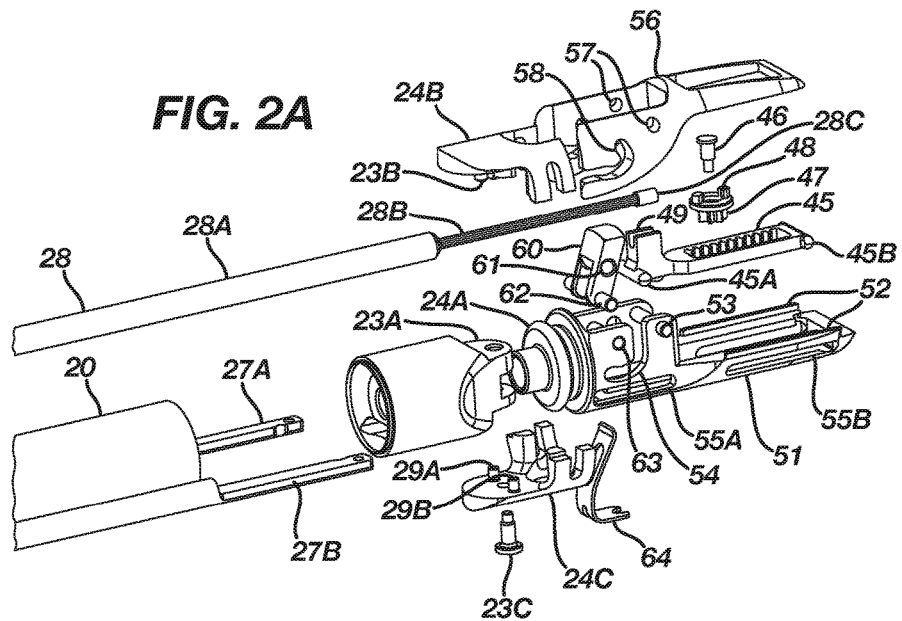
FIG. 2A depicts top perspective exploded view of a cartridge receiving assembly of the instrument of FIG. 1.
Figure 2B:
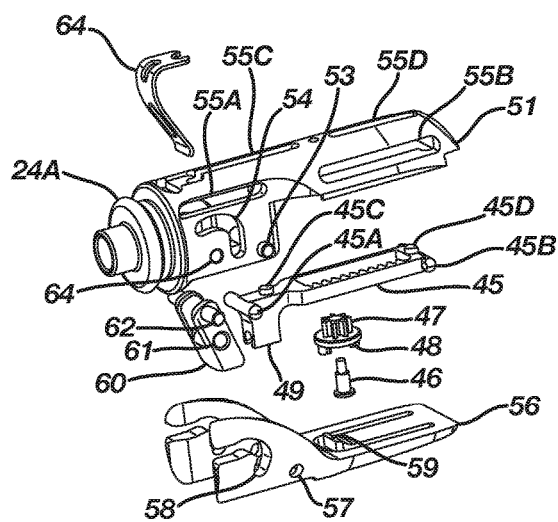
FIG. 2B depicts bottom perspective exploded view of the cartridge receiving assembly of FIG. 2A.

FIGS. 2A-2B illustrate exploded views of cartridge receiving assembly (50) of the present example. Distal end (22) of shaft (20) comprises an articulation joint (23) and a rotational bearing (24). Articulation joint (23) includes a knuckle (23A) that receives pins (23B, 23C), which are connected to bearing supports (24B, 24C). Thus, pins (23B, 2C) define the pivoting axis for articulation joint (23), enabling cartridge receiving assembly (50) to articulate left and right relative the shaft (20), away from the longitudinal axis defined by shaft (20). Rods (27A, 27B) are operably connected to articulation joint (23). In this example, rods (27A, 27B) extend through shaft (20), through knuckle (23A), and connect to pins (29A, 29B) on bearing support (24C). Rods (27A, 27B) are operatively connected to second input (14) to opposingly push and pull rods (27A, 27B). In other words, second input (14) is operable to drive rods (27A, 27B) at the same time in opposite longitudinal directions, such that rod (27A) will translate distally while rod (27B) translates proximally; and such that rod (27B) will translate distally while rod (27A) translates proximally. Because pins (29A, B) are laterally spaced from the pivoting axis, the simultaneous push and pull action will in turn articulate cartridge receiving assembly (50) about joint (23) relative to shaft (20).

Rotational bearing (24) is positioned distal to articulation joint (23). Bearing (24) includes a circumferential flange (24A) that is captured between the bearing supports (24B, 24C) such that the flange (24A) can rotate relative the bearing supports (24B, 24C) and enabling unbounded rotation of cartridge receiving assembly (50) relative shaft (20) about the longitudinal axis defined by shaft (20). A drive rod (28) extends through shaft (20). In this example, drive rod (28) comprises a proximal rigid portion (28A) and a distal bendable portion (28B) that are fixedly connected to one another. Bendable portion (28B) extends through articulation joint (23) and through bearing (24); distal end (28C) is fixedly connected to a mount (49) on a rack (45).

Rack (45) reciprocates longitudinally in lower jaw (51) with followers (45A, 45B, 45C, 45D) constrained in tracks (55A, 55B, 55C, 55D), respectively. Tracks (55A, 55B, 55C, 55D) open through lower jaw (51), providing fluid passages to the internal components within the lower jaw (51), thus facilitating easier cleaning. A pinion (47) is mounted to lower jaw (51) by the pin (46) in the rack (45) such that longitudinal reciprocation of the rack (45) is converted into rotational reciprocation of pinion (47). A key (48) communicates the reciprocating rotation to a rotary input (94) in cartridge body (90), which in turn actuates needle applier cartridge (30).

Drive rod (28) is operatively connected to first input (12) and to third input (16). Actuation of first input (12) will impart axial push and pull loads on drive rod (28) to longitudinally reciprocate rack (45) and thereby actuate needle applier cartridge (30). Actuation of third input (16) will impart a rotational load on drive rod (28) thus rotating cartridge receiving assembly (50) about bearing (24) relative to shaft (20). Accordingly, a single drive rod (28) operates to both actuate needle applier cartridge (30) as well as control distal rotation of needle applier cartridge (30) about the longitudinal axis of shaft (20). By consolidating dual functions with a single drive rod (28), the number of components is reduced, and more space is provided in the shaft (20), which may make the device less expensive to manufacture and easier to clean.

Cartridge receiving assembly (50) is dimensioned and adapted to receive and hold cartridge body (90). As shown in FIGS. 2A-2B, cartridge receiving assembly (50) of this example has upper and lower jaws (56, 51) that are operable to transition between an open configuration and a closed configuration. In the closed configuration, jaws (56, 51) are operable to receive and retain cartridge body (90). In the open configuration, jaws (56, 51) are operable to release cartridge body (90). In the present example, lower jaw (51) is stationary and upper jaw (56) pivots. Alternatively, the arrangement could be reversed, or in some versions both jaws (56, 51) could pivot. Lower jaw (51) has two laterally offset longitudinal rails (52) that are dimensioned and adapted to receive cartridge body (90). Rails (52) help longitudinally align cartridge body (90) in cartridge receiving assembly (50) and laterally retain cartridge body (90) in jaws (51, 56). Upper jaw (56) pivots relative lower jaw (51) about a pin (53) that is received in holes (57). A tooth (59) is resiliently oriented downwardly from upper jaw (56) toward lower jaw (51) with a ramped distal face and a stepped proximal face. Tooth (59) is dimensioned and adapted to latch with cartridge body (90) and longitudinally retain cartridge body (90) in jaws (51, 56). Tooth (59) deflects by virtue of a resilient cantilevered arm extending proximally from the distal end of upper jaw (56). In this example, tooth (59) and the cantilevered arm are monolithic with upper jaw (56), thus reducing the number of components and moving pieces, which may make the device less expensive to manufacture and easier to clean.

A button (60) is operable to open and close jaws (51, 56). While button (60) could be placed on or near the handle assembly (10) in some versions, in this example button (60) is positioned adjacent cartridge receiving assembly (50), which eliminates a linkage in shaft (20) thus creating space in shaft (20) and making the device less expensive and easier to clean. The action of button (60) may vary, but in this example button (60) pivots relative to lower jaw (51) about a pin (63) that is received hole (61). A follower (62) is received by cam slots (54, 58). Pivoting button (60) proximally will open jaws (51, 56), while pivoting button (60) distally will close jaws (51, 56). A spring (64) engages and biases button (60) distally. By pulling button (60) proximally, follower (62) will drive cam slot (58) to open upper jaw (56). When button (60) is released, spring (64) will resiliently drive button (60) distally to close upper jaw (56).

Figure 3A:
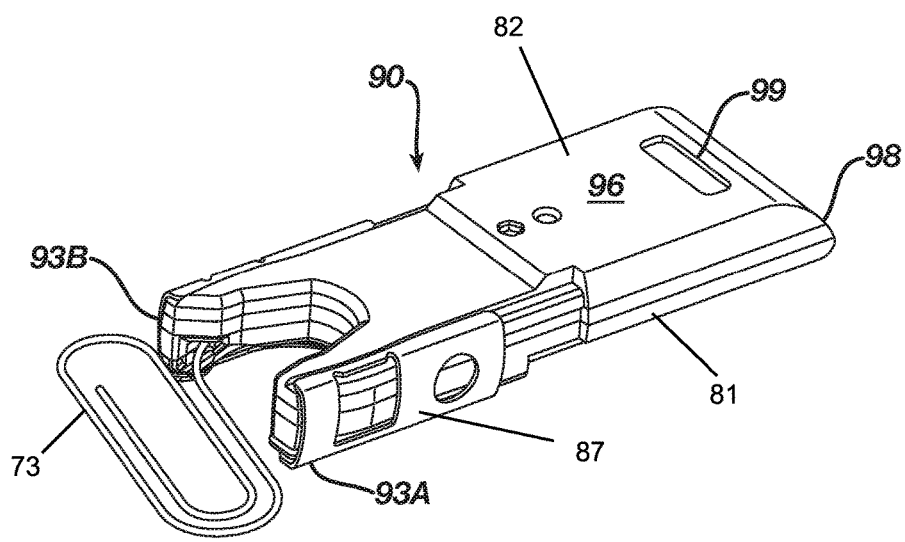
FIG. 3A depicts a top perspective view of an exemplary cartridge configured for receipt in the cartridge receiving assembly of FIG. 2A.
Figure 3B:
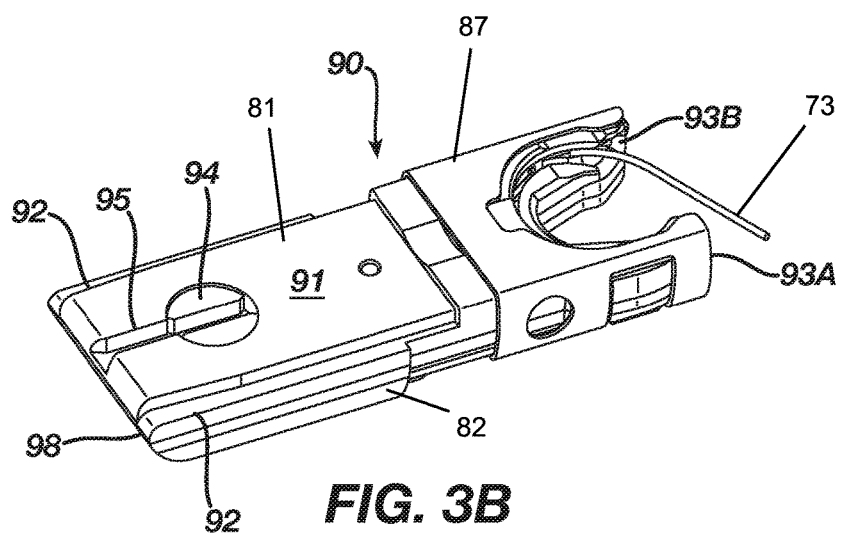
FIG. 3B depicts a bottom perspective view of the cartridge of FIG. 3A.

FIGS. 3A-3B illustrate cartridge body (90) of the present example in greater detail. A lower face (91) of cartridge body (90) is adapted to engage lower jaw (51); and an upper face (96) to engage upper jaw (56). Poke-yoke features on cartridge body (90) prevent improper insertion of cartridge body (90) into cartridge receiving assembly (50), but also contribute to the aesthetic appearance of cartridge body (90). For instance, lower face (91) has a pair of longitudinal notched shoulders (92) that are dimensioned to interface and mate with rails (52). In this example, notched shoulders (92) are shaped as a stepped rabbet, but a variety of other aesthetic shapes could also be employed such as chamfers and radii. In contrast, upper face (96) is asymmetrical relative lower face (91) and lacks shoulder notches, so upper face (96) would interfere with rails (52) if cartridge body (90) were inserted upside-down in cartridge receiving assembly (50). In another instance, the geometry of a proximal face (98) of cartridge body (90) is vertically asymmetrical and thus prevents cartridge body (90) from being inserted upside-down between jaws (51, 56). In this example, proximal face (98) comprises a curved surface that gently transitions to upper face (96), which matches similar geometry in cartridge receiving assembly (50); while the transition to lower face (91) has a tighter radius. Of course, a variety of other asymmetrical aesthetic geometries could also be employed that could contribute to the visual appearance and/or poke-yoke aspects of cartridge body (90).

Arms (93A, 93B) define a generally U-shaped distal end on cartridge body (90). A slot (95) and rotary input (94) are aligned and dimensioned to receive the key (48) while cartridge body (90) is being slid into cartridge receiving assembly (50). When cartridge body (90) is fully seated into cartridge receiving assembly (50), a step (99) aligns with and receives tooth (59) to latch cartridge body (90) in cartridge receiving assembly (50). Key (48) also aligns with rotary input (94), thereby providing a torsional interface that rotationally couples pinion (47) and rotary input (94). In use, the needle (70) exits arm (93A) and enters arm (93B).

Figure 4:
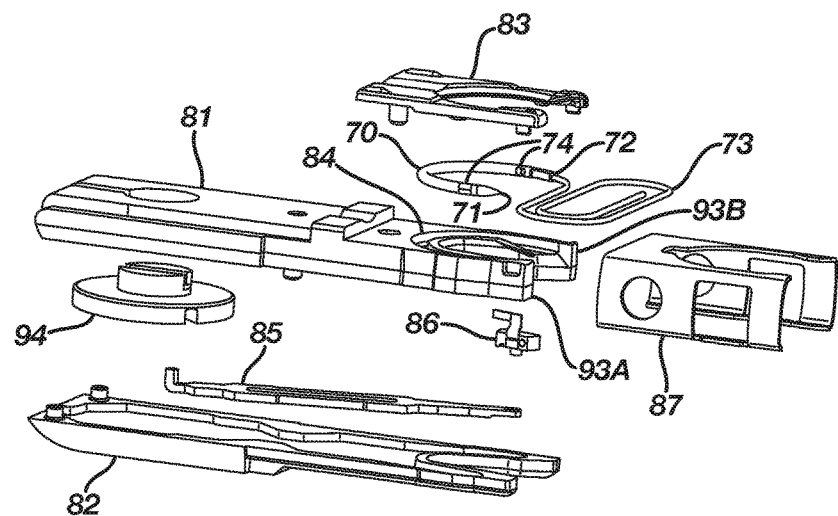
FIG. 4 depicts an exploded view of the cartridge of FIG. 3A.

As shown in FIGS. 3A-4, cartridge body (90) further comprises a lower body (81), an upper body (82), a needle (70), and a needle cover (83). Needle driver (86), rotary input (94), and a link (85) are captured between lower body (81) and upper body (82). Bodies (81, 82) may be attached to one another using a variety of known techniques, including welds, pins, adhesives, and the like to form cartridge body (90). Needle (70) has a leading end (71) and a length of suture (73) extending from the trailing end (72). Needle (70) orbits in a circular path defined by a needle track (84) and between arms (93A, 93B). Needle (70) includes notches (74) that are configured to facilitate engagement between needle driver (86) and needle (70). Needle (70) is captured in needle track (84) by needle cover (83). A cage (87) slides over bodies (81, 82) and needle cover (83) to attach needle cover (83) against lower body (81).

Figure 5A:
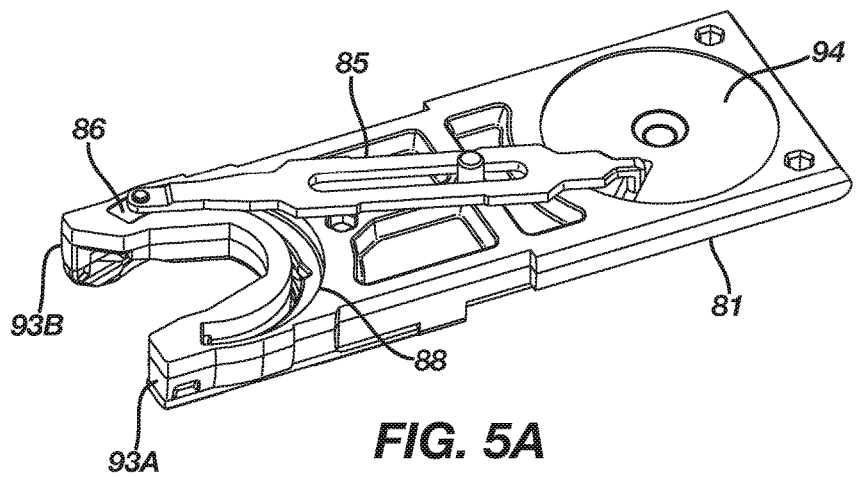
FIG. 5A depicts a perspective view of a drive assembly of the cartridge of FIG. 3A, with the drive assembly at one end of its stroke.
Figure 5B:
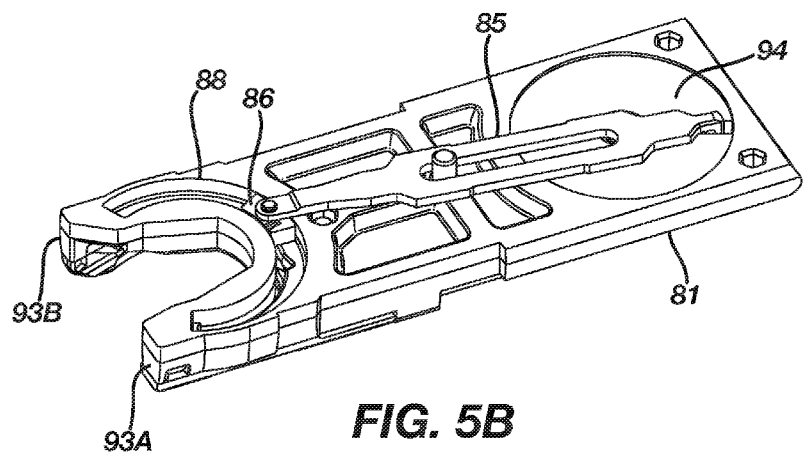
FIG. 5B depicts a perspective view of the drive assembly of FIG. 5A, with the drive assembly at mid-stroke.
Figure 5C:
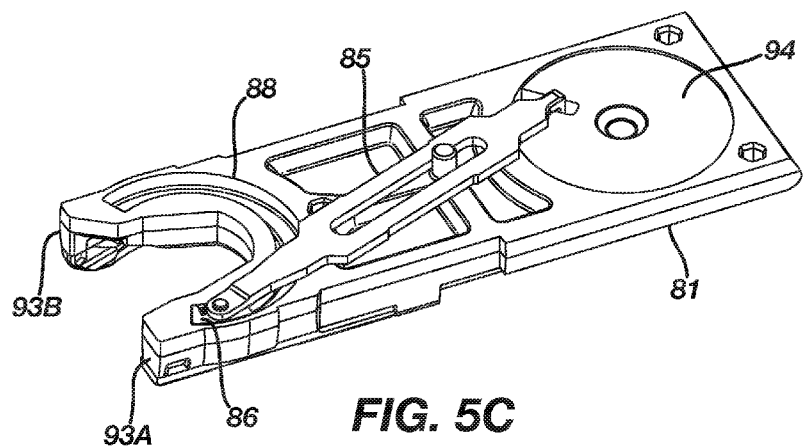
FIG. 5C depicts a perspective view of the drive assembly of FIG. 5A, with the drive assembly at the other end of its stroke.

FIGS. 5A-5C illustrate an example of a drive stroke of the transmission in cartridge body (90) for driving needle (70) in a circular, orbital path. However, it should be understood that needle (70) and suture (73) omitted from FIGS. 5B-5C. Needle driver (86) rides in a carrier track (88) and extends into needle track (84) to engage and drive needle (70). A link (85) connects rotary input (94) to needle driver (86). FIG. 5A shows needle driver (86) positioned at one end of its stroke in carrier track (88). As shown in FIG. 5B, counterclockwise rotation of rotary input (94) will translate needle driver (86) clockwise along carrier track (88), thereby driving needle (70) clockwise. As shown in FIG. 5C, continued counterclockwise rotation of the rotary input (94) will continue to translate needle driver (86) and thereby drive needle (70) clockwise until it reaches the other end of its stroke in carrier track (88). In this example, the drive stroke rotates the needle (70) in its circular path along an angular range of about 180 degrees. For the return stroke, the sequence can be reversed by rotating the rotary input (94) clockwise, which will translate needle driver (86) counterclockwise in carrier track (88). Needle driver (86) is disengaged from needle (70) during the return stroke until needle driver (86) reaches the end of the return stroke. Needle driver (86) will re-engage needle (86) upon completing the return stroke. Thus, a sequence of drive and return strokes will rotate the needle (70) in a circular path.

Figure 6:
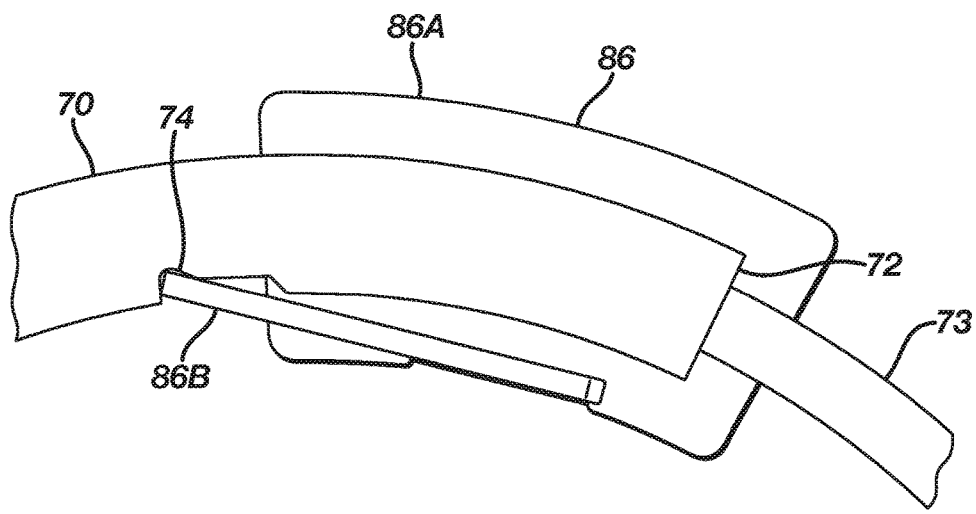
FIG. 6 depicts a partial plan view of a needle driver of the cartridge of FIG. 3A engaging a needle of the cartridge of FIG. 3A.

FIG. 6 illustrates a detailed view of needle driver (86) engaging needle (70). Needle driver (86) comprises a carrier (86A) and a driver (86B). Carrier (86A) is dimensioned to slideably fit in carrier track (88). Driver (86B) is attached to carrier (75) and is operative to engage needle (70) at an oblique angle. Leftward movement of needle driver (86) will cause driver (86B) to engage proximal notch (74) of needle (70) during the drive stroke. When so engaged, needle (70) will slide in needle track (84) in unison with needle driver (86). Due to the oblique angle, rightward movement of needle driver (86) will disengage driver (86B) from proximal notch (74) of needle (70) and slide over the stationary needle (70) during the return stroke.

Referring back to FIGS. 5A-5C, when first input (12) is depressed, closing the trigger, needle driver (86) will be actuated through its drive stroke where it orbits along an angular range of motion at least about 180 degrees counterclockwise to a driven position as shown in FIG. 5C. During the drive stroke, driver (86B) engages proximal notch (74) and will in unison rotate needle (70) about 180 degrees along an orbital path to its extended position. Needle (70) will span across arms (93A, 93B) between exit port (95) and entrance port (97). Tissue interposed between arms (93A, 93B) will be pierced by leading end (71) of needle (70).

When first input (12) is released and the spring return opens the trigger, needle driver (86) reciprocates through its return stroke where it orbits along an angular range of motion about 180 degrees clockwise back to the return position shown in FIG. 5A. During the return stroke, driver (86B) slides over the needle (70). Driver (86B) is then adjacent the distal notch (74). When first input (12) is depressed again closing the trigger, needle driver (86) will again be actuated through its drive stroke where it orbits along an angular range of motion about 180 degrees counterclockwise to the driven position as shown in FIG. 5C. During the drive stroke, driver (86B) engages distal notch (74) and will in unison drive needle (70) orbitally along an angular range of motion about 180 degrees back to its retracted position. Suture (73) will follow needle (70) and be threaded through the pierced tissue.

When first input (12) is again released and the spring return opens the trigger, needle driver (86) again reciprocates through its return stroke where it orbits along an angular range of motion about 180 degrees clockwise back to its returned position as shown in FIG. 5A. During the return stroke, driver (86B) slides over needle (70). Thus, needle (70) is driven in a complete circular path spanning an angular range of 360° in response to first input (12) being actuated twice. The sequence may be repeated as needed by the surgeon to achieve the desired suturing task.

Further details, explanations, examples, and alternative embodiments of surgical suturing devices and subcomponents of the foregoing are disclosed in U.S. Pub. No. 2014/0171970, entitled "Circular Needle Applier with Articulating and Rotating Shaft," published Jun. 19, 2014 now U.S. Pat. No. 9,357,998, issued Jun. 7, 2016, the disclosure of which is incorporated by reference herein; U.S. patent application Ser. No. 14/297,993, entitled "Jawed Cartridge Receiving Assembly for Needle Cartridge," filed Jun. 6, 2014, now U.S. Pat. No. 9,474,522, issued Oct. 25, 2016, the disclosure of which is incorporated by reference herein; and U.S. patent application Ser. No. 14/298,038, entitled "Circular Needle Applier with Cleats," filed Jan. 30, 2015, now U.S. Pat. No. 9,375,212 on Jun. 28, 2016, the disclosure of which is incorporated by reference herein. It should be understood that such details, explanations, examples, and alternative embodiments may be readily applied to the above-described instrument (10) and subcomponents thereof.

II. Exemplary Elastomeric Cleat

In some instances, it may be desirable to utilize features to restrict the orbital motion of needle (70) to one angular direction. For instance, it may be desirable to engage multiple sides of needle (70) rather than just one lateral side or just one side at the outer curvature of needle (70). Additionally, engaging needle (70) on two lateral sides may further prevent needle (70) from deviating off needle track (84), possibly helping further stabilize needle (70) within a single plane of orbital motion.

FIGS. 7A-8C show an exemplary alternative cartridge body (190) that is configured to drive a needle (170) in an orbital motion limited to one angular direction. Cartridge body (190) may be incorporated into a cartridge that is configured and operable just like cartridge (30) described above, except for the differences described below. It should therefore be understood that cartridge receiving assembly (50) may readily receive and operate a cartridge incorporating cartridge body (190), such that cartridge body (190) may be used in instrument (2) in accordance with the teachings above.

Needle (170) is substantially similar to needle (70) described above. Cartridge body (190) is substantially similar to cartridge body (90) described above. However, unlike cartridge body (90), cartridge body (190) of the present example contains elastomeric cleats (176, 177). While not shown, it should be understood that cartridge body (190) contains needle driver (86), which rides in carrier track (88) and extends into needle track (184) to engage and drive needle (170). Needle track (184) is substantially similar to needle track (84) described above. Therefore, needle track (184) is located adjacent to lower body (181). Additionally, cartridge body (191) contains lower body (181), and arms (193A, 193B) helping define exit port (195) and entrance port (197). Lower body (181), arms (193A, 193B), exit port (195), and entrance port (197) are substantially similar to lower body (81), arms (93A, 93B), exit port (95), and entrance port (97) described above.

Figure 7A:
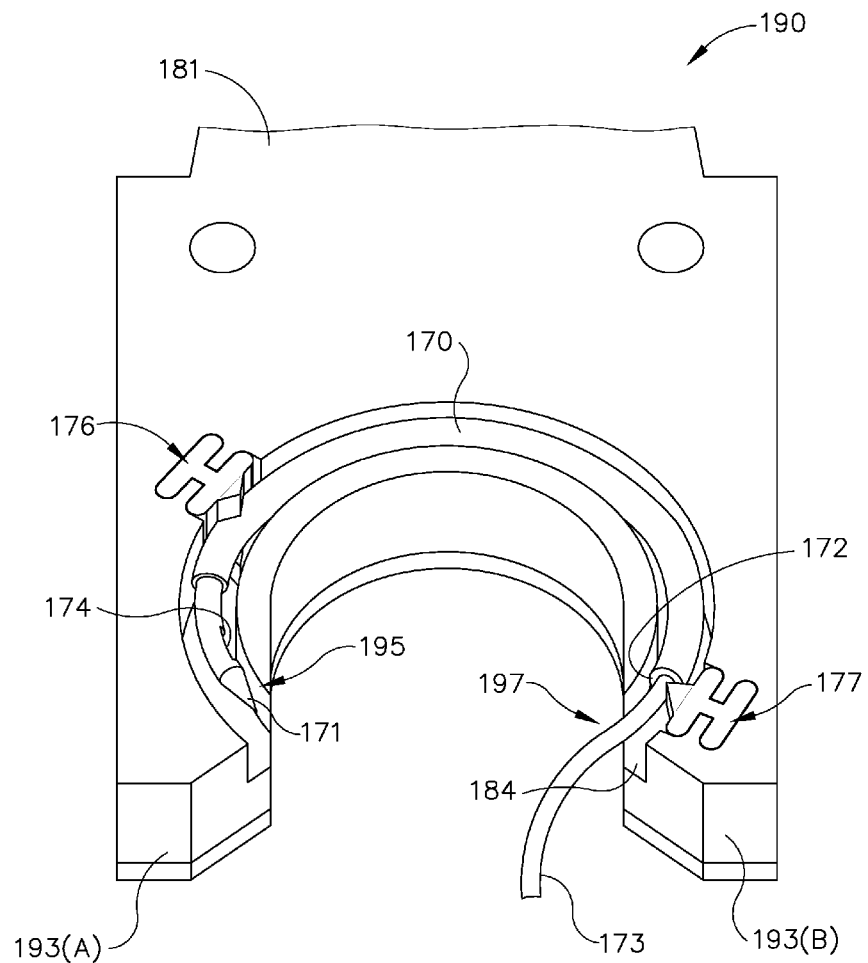
FIG. 7A depicts a perspective view of an exemplary alternative cartridge configured for receipt in the cartridge receiving assembly of FIG. 2A, with a portion of the cartridge removed to reveal a needle in a retracted position.
Figure 7B:
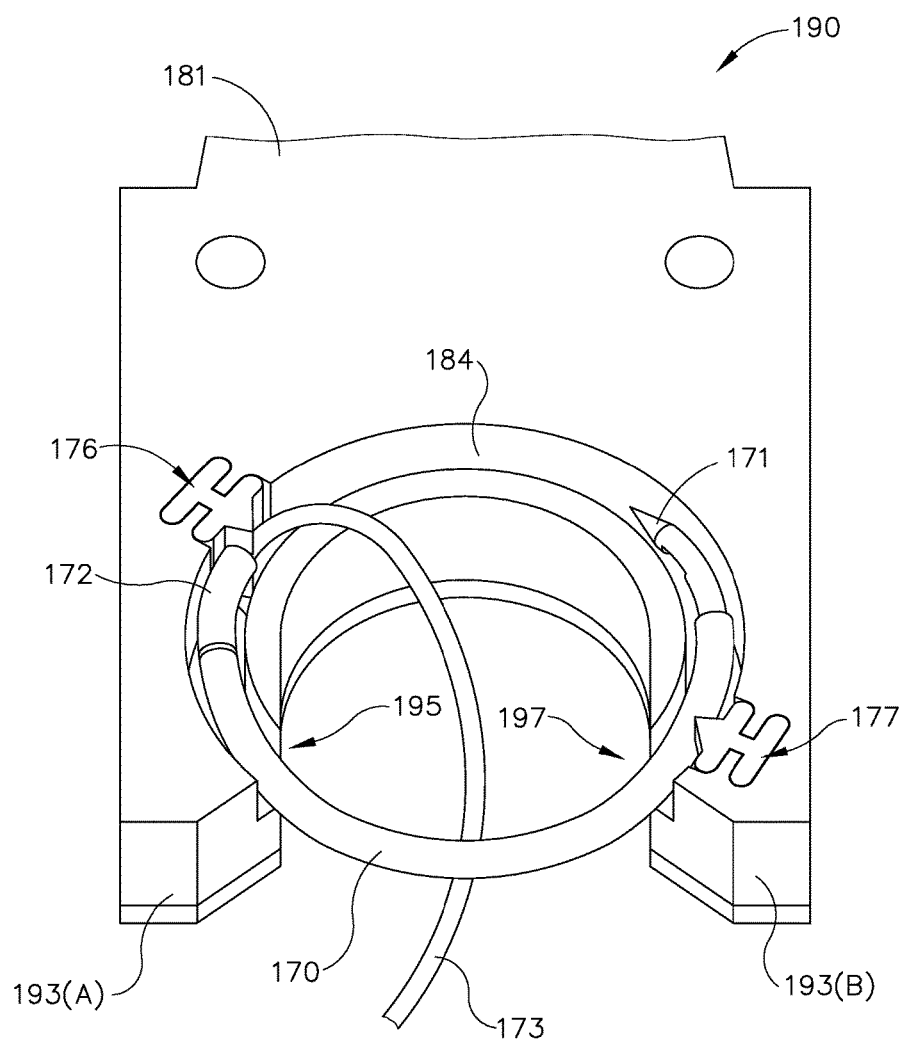
FIG. 7B depicts a perspective view of the cartridge of FIG. 7A, with the needle in an extended position.

FIGS. 7A-B show how cleats (176, 177) engage needle (170) through the orbital travel of needle (170). Cleats (176, 177) are located along lower body (181) so that either an individual cleat (176, 177) or both cleats (176, 177) engage needle (170) regardless of where needle (170) is located along its orbital path. It is important to note that cleats (176, 177) are located on lower body (181) at the exterior of the arc defined by needle track (184). Therefore, notches (174) that interface with needle driver (86) may be located on the interior of the arc defined by needle (170) in order to drive needle (170).

FIG. 7A shows the distal end of cartridge body (190) when needle applier cartridge (30) is in an initial state. It should be understood that the state shown in FIG. 7A corresponds with the state shown in FIG. 5A. Needle (170) is in its retracted position and completely contained in needle track (184). Cleat (176) resiliently engages needle (70), while cleat (177) is adjacent to trailing end (172), preventing needle (170) from rotating clockwise.

Needle (170) may be rotated by needle driver (86) counterclockwise to the position shown in FIG. 7B by the methods and components described above. When needle (170) is in the position shown in FIG. 7B, cleat (177) now resiliently engages needle (170), while cleat (176) is now adjacent to trailing end (172), preventing needle (170) from rotating clockwise. Additionally, needle (170) may be rotated along the orbital path by needle driver (86) further counterclockwise from the position of FIG. 7B to the position of FIG. 7A by the methods and components described above.

Figure 8A:
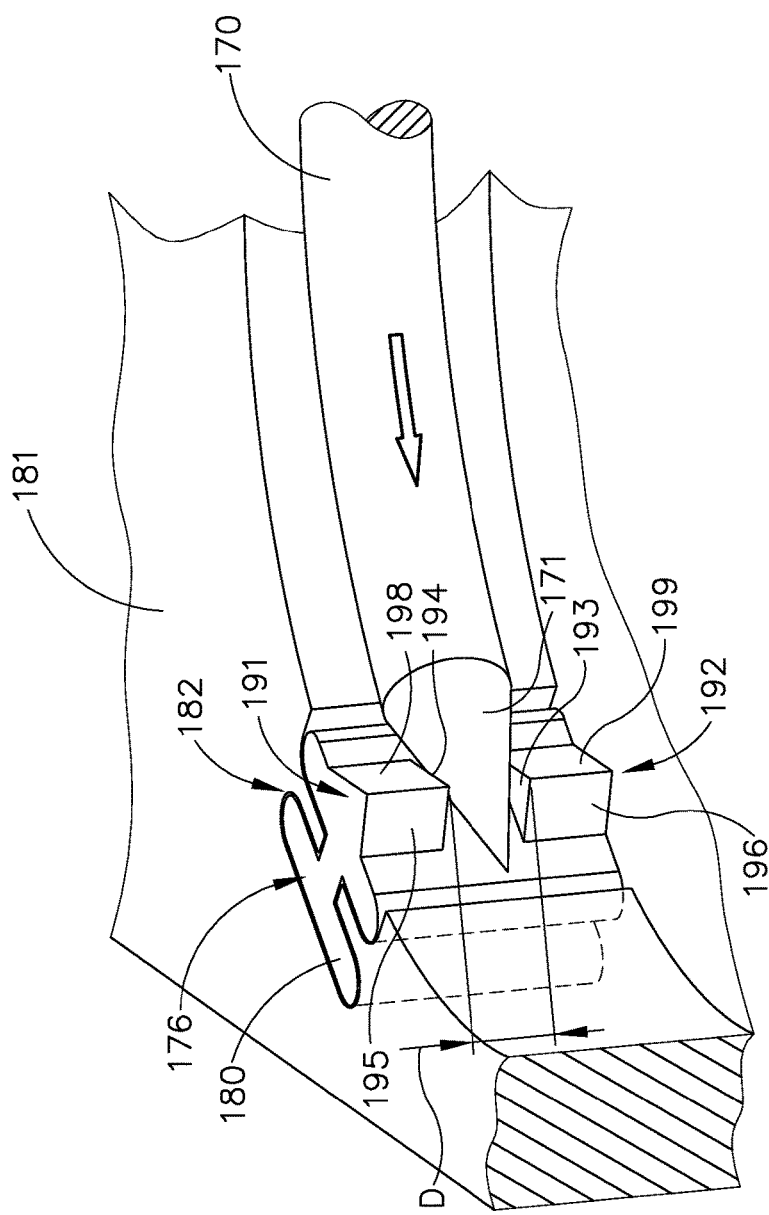
FIG. 8A depicts an enlarged perspective view of an elastomeric cleat of the cartridge of FIG. 7A, with a sharp tip of the needle engaging the cleat.
Figure 8B:
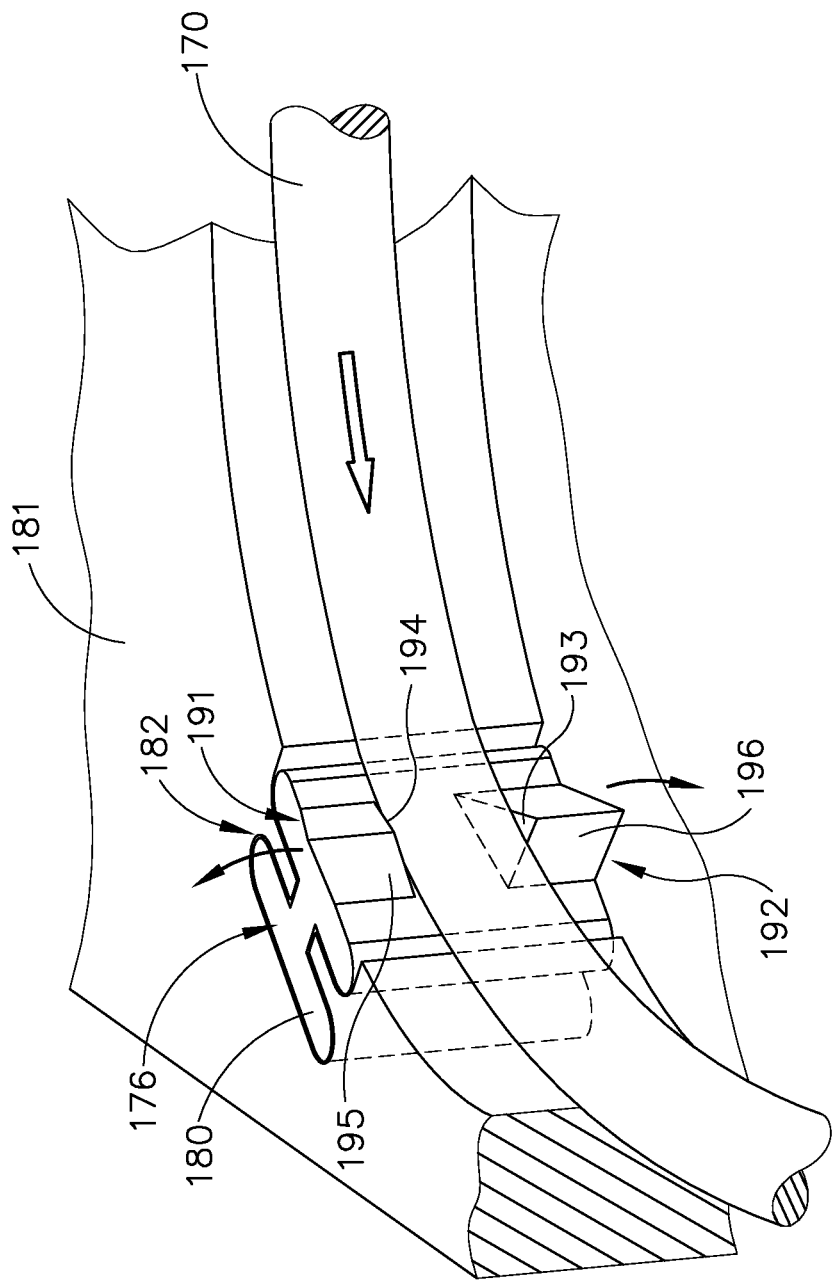
FIG. 8B depicts an enlarged perspective view of the cleat of FIG. 8A, with a mid-section of the needle engaging the cleat.

FIGS. 8A-C show how cleats (176, 177) engage needle (170) in order to restrict the orbital motion of needle (170) to one angular direction, and to further stabilize the planar positioning if needle (170) within needle track (184), by engaging needle (170) on two lateral sides of needle (170) (i.e., on sides that are lateral to the arc or curvature followed by needle (170)). Lower body (181) includes complementary recesses (182) that are positioned where cleats (176, 177) are to be located. Complementary recesses (182) are configured to receive an insert portion (180) of each cleat (176, 177) to thereby secure cleats (176, 177) to lower body (181). Insert portion (180) and complementary recess (182) are dimensioned to have an interference fit, thereby fixing insert portion (180) relative to lower body (181). However, other suitable means of attaching cleat (176, 177) to lower body (181) will be apparent to one having ordinary skill in the art in view of the teachings herein.

Cleats (176, 177) are made from an elastomeric material having resilient properties. By way of example only, cleats (176, 177) may comprise rubber, silicone, and/or any other suitable resilient elastomeric material. Each cleat (176, 177) includes an insert portion (180), an upper resilient stud (191), and a lower resilient stud (192). As noted above, insert portions fit in complementary recesses (182) of lower body (181) to thereby secure cleats (176, 177) to lower body (181). Resilient studs (191, 192) are capable of being deflected from a relaxed position (FIGS. 8A, 8C) to a deformed position (FIG. 8B). Resilient studs (191, 192) extend inwardly from lower body (181) toward needle track (184). Upper resilient stud (191) further includes an interior face (194), an adjacent abutting surface (195), and an obliquely angled surface (198). Similarly, lower resilient stud (192) further includes an interior face (193), an adjacent abutting surface (196), and an obliquely angled surface (198). Interior faces (194, 193) are directed toward each another, thereby defining a predetermined gap (D) when resilient studs (191, 192) are in a relaxed position. Abutting surfaces (195, 196) are transverse to respective interior faces (194, 193) and face toward the direction of orbital rotation of needle (170). Angled surfaces (198, 199) are obliquely oriented relative to respective abutting surfaces (195, 196).

Predetermined gap (D) is sized to be larger than the diameter of leading end (171) of needle (170), but smaller than the diameter of trailing end (172) of needle (170) and the intermediate region of needle (170). Of course, needle (170) need not have a circular cross sectional area. Needle (170) may be of any shape suitable, so long at the dimensions of leading end (171) and trailing end (172) of needle (170) have the above noted relationship with predetermined gap (D).

FIG. 8A shows leading end (171) of needle (170) entering between interior faces (194, 193). As can be seen, leading end (171) is dimensioned to fit within predetermined gap (D) defined by interior faces (194, 193) when resilient studs (191, 192) are in a relaxed position. As needle (170) is driven along an orbital path as described above leading end (171) rotates further in the counter clockwise direction, such that the diameter of needle (171) positioned between interior faces (194, 193) increases. As the diameter of needle (171) positioned between interior faces (194, 193) increases, needle (170) begins to contact interior faces (194, 193), therefore transitioning resilient studs (191, 192) from a relaxed position to a deformed position.

FIG. 8B shows resilient studs (191, 192) in a deformed position due to contact between needle (170) and interior faces (194). This is the position associated with cleat (176) while needle (170) is positioned within needle track (184) as shown in FIG. 7A. It is important to note that both interior faces (194, 193) are in contact with needle (170). Because cleats (176, 177) are made of elastomeric material having resilient properties, the deflected studs (191, 192) resiliently bear inwardly against the exterior of needle (170) in opposing directions toward the central axis of needle (170). These opposing inward forces exerted on needle (170) may help force needle (170) to remain on a single plane defined by the orbital path of needle (170). Therefore, needle (170) is less inclined to deviate from the plane defined by the orbital path of needle (170). However, the spring like force exerted on needle (170) is not so great as to inhibit needle drive (86) from rotating needle (170) along the orbital path. The opposing inward forces imparted by resilient studs (191, 192), in addition to friction imposed by the elastomeric material of studs (191, 192), may also prevent needle (170) from moving in an angular direction opposite to the angular direction of the driven orbital path of needle (170). In other words, cleats (176, 177) ensure that the orbital motion of needle (170) is in just one single angular direction.

Eventually, needle (170) travels past interior faces (194, 193) as shown in FIG. 8C. This is the position associated with cleat (176) while needle (170) is positioned within needle track (184) as shown in FIG. 7B. At this point, needle (170) is no longer deflecting interior faces (194,193) of resilient studs (191, 192) away from each other. Because needle (170) and resilient studs (191, 192) are no longer in contact, the resilient nature of the elastomeric material allows resilient studs (191, 192) to transition from a deformed position back to the relaxed position. Because resilient studs (191, 192) are in a relaxed position, interior faces (194, 193) are back in a position to define predetermined gap (D). As mentioned above, predetermined gap (D) is sized smaller than the diameter of trail end (172) of needle (170). Because predetermined gap (D) is smaller than the diameter of trailing end (172), abutting surfaces (195, 196) will contact trailing end (172) if needle (170) attempts to travel in the opposite angular direction, thereby restricting orbital travel of needle (170) to one direction. In other words, at the stage shown in FIG. 8C, cleats (176, 177) ensure that the orbital motion of needle (170) is in just one single angular direction.

It is important to note that while cleat (176) is discussed in reference to FIGS. 8A-8C above, cleat (177) operates in the same manner. Therefore, needle (170) is limited to one plane of orbital direction as well as one angular direction. Referring back to FIG. 7A, cleat (177) is in a state similar to that shown in FIG. 8C while cleat (176) is in a state similar to that shown in FIG. 7B. Referring back to FIG. 7B, cleat (176) is in a state similar to that shown in FIG. 8C while cleat (177) is in a state similar to that shown in FIG. 8B. It should be understood that as needle (170) orbits as described above, suture (173) may pass through the gap between studs (191, 192) at least during the stage shown in FIG. 8C. The size of predetermined gap (D) may be sufficiently larger than the outer diameter of suture (173) such that cleats (176, 177) do not bind against or otherwise interfere with suture (173).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical instrument comprising: (a) a cartridge receiving assembly; (b) a shaft assembly, wherein the shaft assembly comprises: (i) a distal end, wherein the cartridge receiving assembly is positioned at the distal end of the shaft assembly, and (ii) a first actuation member; (c) a needle driving cartridge, comprising: (i) a body, (ii) a curved needle, wherein the curved needle has an outer surface and a length, (iii) a needle drive assembly operable to drive the curved needle along an orbital path, and (iv) a needle guide assembly comprising a needle track partially defining the orbital path, wherein the needle guide assembly is operable to guide the curved needle along the orbital path, wherein the needle guide assembly comprises a first cleat, wherein the first cleat comprises two needle engagement features, wherein the two needle engagement features are configured to simultaneously engage two separate regions of the outer surface of the needle at a first portion of the length of the needle; wherein the cartridge receiving assembly is operable to receive the needle driving cartridge, wherein the first actuation member is operable to actuate the cartridge receiving assembly to thereby drive the needle drive assembly.

EXAMPLE 2

The surgical instrument of Example 1, wherein the first cleat is operable to restrict the curved needle to travel in one angular direction along the orbital path.

EXAMPLE 3

The surgical instrument of any one or more of Examples 1 through 2, wherein the first cleat is configured contact the curved needle on two lateral regions of the outer surface of the needle while the needle travels along the orbital path.

EXAMPLE 4

The surgical instrument of any one or more of Examples 1 through 3, wherein the first cleat extends from the body toward the needle track.

EXAMPLE 5

The surgical instrument of any one or more of Examples 1 through 4, wherein the first cleat comprises elastomeric material.

EXAMPLE 6

The surgical instrument of any one or more of Examples 1 through 5, wherein the first cleat is attached to the body.

EXAMPLE 7

The surgical instrument of Example 6, wherein the first cleat further comprises an insert, wherein the body further comprises a complementary recess configured to receive the insert, wherein the insert and complementary recess attach the first cleat to the body.

EXAMPLE 8

The surgical instrument of any one or more of Examples 1 through 7, wherein the first cleat further comprises a first resilient stud and a second resilient stud.

EXAMPLE 9

The surgical instrument of Example 8, wherein the first resilient stud is above the second resilient stud relative the plane of the orbital path of the needle.

EXAMPLE 10

The surgical instrument of any one or more of Examples 8 through 9, where the first resilient stud and the second resilient stud extend from the body toward the needle track.

EXAMPLE 11

The surgical instrument of any one or more of Examples 8 through 10, wherein the first resilient stud and the second resilient stud are configured to transition between a first position and a second position, wherein the first resilient stud is parallel with the second resilient stud in the first position, wherein the first resilient stud is not parallel with the second resilient stud in the first position.

EXAMPLE 12

The surgical instrument of any one or more of Examples 8 through 11, wherein the first resilient stud comprises a first interior surface and a first abutting surface, wherein the second resilient stud comprises a second interior surface and a second abutting surface, wherein the first interior surface and the second interior surface face toward each other, wherein the first abutting surface and the second abutting surface face in the same direction.

EXAMPLE 13

The surgical instrument of Example 12, wherein the needle is configured to travel along its orbital path between the first interior surface and the second interior surface.

EXAMPLE 14

The surgical instrument of any one or more of Examples 12 through 13, wherein the first interior surface is configured to contact the curved needle on a first lateral surface, wherein the second interior surface is configured to contact the need on a second lateral surface, thereby simultaneously contacting the curved needle on two lateral surfaces of the needle while the needle travels along the orbital path.

EXAMPLE 15

The surgical instrument of Example 14, wherein the needle is configured to transition the first resilient stud and the second resilient stud from the first position to the second position when the needle travels along its orbital path between the first interior surface and the second interior surface.

EXAMPLE 16

The surgical instrument of Example 15, wherein the needle defines a thickness, wherein the first interior surface and the second interior surface define a gap distance when first resilient stud and second resilient stud are in the first position, wherein the gap distance is smaller than the thickness of the needle.

EXAMPLE 17

The surgical instrument of any one or more of Examples 15 through 16, wherein the first resilient stud and the second resilient stud are configured to be in the first position when the needle is not positioned between the first interior surface and the second interior surface.

EXAMPLE 18

The surgical instrument of any one or more of Examples 1 through 17, wherein the needle guide assembly further comprises a second cleat, wherein the second cleat is configured to engage the outer surface of the needle at a second portion of the length of the needle while the first cleat engages the first portion of the length of the needle.

EXAMPLE 19

A needle driving cartridge, comprising: (a) a body; (b) a curved needle, wherein the curved needle has an outer surface and defines a curved central axis; (c) a suture attached to the needle; (d) a needle drive assembly operable to drive the curved needle along an orbital path; and (e) a needle guide assembly comprising a needle track partially defining the orbital path, wherein the needle guide assembly is operable to guide the curved needle along the orbital path, wherein the needle guide assembly comprises a cleat, wherein the cleat comprises two resilient studs, wherein the resilient studs are configured to resiliently bear inwardly against the two separate regions of the outer surface of the needle toward the curved central axis of the needle.

EXAMPLE 20

A surgical instrument comprising: (a) a cartridge receiving assembly; (b) a shaft assembly, wherein the shaft assembly comprises: (i) a distal end, wherein the cartridge receiving assembly is positioned at the distal end of the shaft assembly, and (ii) a first actuation member; (c) a needle driving cartridge, comprising: (i) a body, (ii) a curved needle, (iii) a needle drive assembly operable to drive the curved needle along an orbital path, and (iv) a needle guide assembly comprising an elastomeric member attached to the body, wherein the elastomeric member further comprises a first flange and a second flange extending from the body toward the orbital path, wherein the first flange and the second flange are operable to transition from a first position to a second position, wherein the first flange and the second flange are parallel to each other in the first position, wherein the first flange and the second flange are non-parallel to each other in the second position, wherein the needle is configured to drive the first and second flanges to the second position.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A surgical instrument comprising:
 (a) a cartridge receiving assembly;
 (b) a shaft assembly, wherein the shaft assembly comprises:
  (i) a distal end, wherein the cartridge receiving assembly is positioned at the distal end of the shaft assembly, and
  (ii) a first actuation member;
 (c) a needle driving cartridge, comprising:
  (i) a body,
  (ii) a curved needle, wherein the curved needle has an outer surface and a length,
  (iii) a needle drive assembly operable to drive the curved needle along an orbital path, and
  (iv) a needle guide assembly comprising a needle track partially defining the orbital path, wherein the needle guide assembly is operable to guide the curved needle along the orbital path, wherein the needle guide assembly comprises a first cleat, wherein the first cleat comprises two needle engagement features, wherein the two needle engagement features comprise a first resilient stud and a, second resilient stud, wherein the first resilient stud comprises a first interior surface, wherein the second resilient stud comprise a second interior surface facing toward the first interior surface, wherein the first interior surface and the second interior surface are configured to flex between a first position and a second position in response to the curved needle travelling along the orbital path via the needle assembly, wherein the first interior surface and the second interior surface are parallel relative to each other in the first position and define a predetermined gap therebetween in the first position, wherein the first interior surface and the second interior surface are non-parallel relative to each other in the second position, wherein the two needle engagement features are configured to simultaneously engage two separate regions of the outer surface of the needle at a first portion of the length of the needle;

wherein the cartridge receiving assembly is operable to receive the needle driving cartridge, wherein the first actuation member is operable to actuate the cartridge receiving assembly to thereby drive the needle drive assembly.

2. The surgical instrument of claim 1, wherein the first cleat is operable to restrict the curved needle to travel in one angular direction along the orbital path.

3. The surgical instrument of claim 1, wherein the first cleat is configured to contact the curved needle on two lateral regions of the outer surface of the needle while the needle travels along the orbital path.

4. The surgical instrument of claim 1, wherein the first cleat extends from the body toward the needle track.

5. The surgical instrument of claim 1, wherein the first cleat comprises elastomeric material.

6. The surgical instrument of claim 1, wherein the first cleat is attached to the body.

7. The surgical instrument of claim 6, wherein the first cleat further comprises an insert, wherein the body further comprises a complementary recess configured to receive the insert, wherein the insert and complementary recess attach the first cleat to the body.

8. The surgical instrument of claim 1, wherein the first resilient stud is above the second resilient stud relative a plane of the orbital path of the needle.

9. The surgical instrument of claim 1, where the first resilient stud and the second resilient stud extend from the body toward the needle track.

10. The surgical instrument of claim 1, wherein the first resilient stud comprises a first abutting surface, wherein the second resilient stud comprises a second abutting surface, wherein the first abutting surface and the second abutting surface face in the same direction.

11. The surgical instrument of claim 10, wherein the needle is configured to travel along its orbital path between the first interior surface and the second interior surface.

12. The surgical instrument of claim 10, wherein the first interior surface is configured to contact the curved needle on a first lateral surface, wherein the second interior surface is configured to contact the needle on a second lateral surface, thereby simultaneously contacting the curved needle on two lateral surfaces of the needle while the needle travels along the orbital path.

13. The surgical instrument of claim 12, wherein the needle is configured to transition the first resilient stud and the second resilient stud from the first position to the second position when the needle travels along its orbital path between the first interior surface and the second interior surface.

14. The surgical instrument of claim 13, wherein the needle defines a thickness, wherein the gap distance is smaller than the thickness of the needle.

15. The surgical instrument of claim 13, wherein the first resilient stud and the second resilient stud are configured to be in the first position when the needle is not positioned between the first interior surface and the second interior surface.

16. The surgical instrument of claim 1, wherein the needle guide assembly further comprises a second cleat, wherein the second cleat is configured to engage the outer surface of the needle at a second portion of the length of the needle while the first cleat engages the first portion of the length of the needle.

17. A surgical instrument comprising:
(a) a cartridge receiving assembly;
(b) a shaft assembly, wherein the shaft assembly comprises:
(i) a distal end, wherein the cartridge receiving assembly is positioned at the distal end of the shaft assembly, and
(ii) a first actuation member;
(c) a needle driving cartridge, comprising:
(i) a body,
(ii) a curved needle,
(iii) a needle drive assembly operable to drive the curved needle along an orbital path, and
(iv) a needle guide assembly comprising an elastomeric member attached to the body, wherein the elastomeric member further comprises a first flange and a second flange extending from the body toward the orbital path, wherein the first flange and the second flange are operable to transition from a first position to a second position, wherein the first flange and the second flange have respective first and second surfaces that face each other in the first position and are parallel to each other in the first position, wherein the first surface and the second surface are non-parallel to each other in the second position, wherein the needle is configured to drive the first and second flanges to the second position in response to the curved needle travelling along the orbital path via the needle drive assembly, wherein the first surface and the second surface define a predetermined gap when in the first position.

18. A surgical instrument comprising:
(a) a cartridge receiving assembly,
(b) a shaft assembly, wherein the shaft assembly comprises:
(i) a distal end, wherein the cartridge receiving assembly is positioned at the distal end of the shaft assembly, and
(ii) a first actuation member;
(c) a needle driving cartridge, comprising:
(i) a body,
(ii) a curved needle, wherein the curved needle has an outer surface and a length,
(iii) a needle drive assembly operable to drive the cured needle along an orbital path, and
(iv) a needle guide assembly comprising a needle track partially defining the orbital path, wherein the needle guide assembly is operable to guide the curved needle along the orbital path, wherein the needle guide assembly comprises a first contact surface and a second contact surface configured to flex, in response to the curved needle traveling along the orbital path via the needle drive assembly from a first position to a second position, wherein the first contact surface and the second contact surface face each other in the first position, are parallel relative to each other in the first position, and define a gap in the first position.

* * * * *